(12) United States Patent
Gray et al.

(10) Patent No.: US 11,491,315 B2
(45) Date of Patent: Nov. 8, 2022

(54) SYSTEMS AND METHODS FOR CREATING PERMANENT DRAINAGE FISTULA

(71) Applicant: Boston Scientific Scimed, Inc., Maple Grove, MN (US)

(72) Inventors: Jeff Gray, Lexington, MA (US); Ryan V. Wales, Northborough, MA (US); Scott E. Brechbiel, Acton, MA (US); Laura E. Christakis, Framingham, MA (US); Paul Smith, Smithfield, RI (US); Sean Fleury, Minneapolis, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1165 days.

(21) Appl. No.: 16/012,111

(22) Filed: Jun. 19, 2018

(65) Prior Publication Data
US 2018/0361127 A1    Dec. 20, 2018

Related U.S. Application Data

(60) Provisional application No. 62/522,348, filed on Jun. 20, 2017.

(51) Int. Cl.
*A61M 27/00* (2006.01)
*A61F 2/04* (2013.01)
(Continued)

(52) U.S. Cl.
CPC ........... *A61M 27/002* (2013.01); *A61B 17/11* (2013.01); *A61B 17/1114* (2013.01);
(Continued)

(58) Field of Classification Search
CPC ............ A61M 27/002; A61M 27/3655; A61M 27/3478; A61M 2025/0233; A61M 2025/0286; A61B 17/11; A61B 17/1114; A61B 17/3478; A61B 18/00; A61B 18/08; A61B 2017/00876; A61B 2017/1139; A61F 2/04; A61F 2/064; A61F 2/848; A61F 2/90; A61F 2002/041; A61F 2002/8483;
(Continued)

(56) References Cited

U.S. PATENT DOCUMENTS 3,874,388 A    4/1975 King et al.
5,234,447 A    8/1993 Kaster et al.
(Continued)

FOREIGN PATENT DOCUMENTS

CN    203291065    11/2013
EP    1894514    3/2008
(Continued)

OTHER PUBLICATIONS

International Search Report and Written Opinion dated (Dec. 19, 2018), for PCT/US18/38238 (22 pages).

*Primary Examiner* — Philip R Wiest
(74) *Attorney, Agent, or Firm* — Seager, Tufte & Wickhem, LLP

(57) ABSTRACT

The present disclosure relates generally to the field of medical devices and establishing fluid communication between body lumens. In particular, the present disclosure relates to devices and methods for placing the muscularis layers of first and second body lumens in contact to establish a long term or permanent open flow or access passage therebetween.

18 Claims, 13 Drawing Sheets

(51) Int. Cl.
  *A61B 17/11* (2006.01)
  *A61F 2/06* (2013.01)
  *A61B 18/00* (2006.01)
  *A61M 1/36* (2006.01)
  *A61F 2/90* (2013.01)
  *A61F 2/848* (2013.01)
  *A61F 2/95* (2013.01)
  *A61B 17/34* (2006.01)
  *A61B 17/00* (2006.01)
  *A61B 18/08* (2006.01)
  *A61M 25/02* (2006.01)

(52) U.S. Cl.
  CPC ............... *A61B 18/00* (2013.01); *A61F 2/04* (2013.01); *A61F 2/064* (2013.01); *A61F 2/848* (2013.01); *A61F 2/90* (2013.01); *A61M 1/3655* (2013.01); *A61B 17/3478* (2013.01); *A61B 18/08* (2013.01); *A61B 2017/00876* (2013.01); *A61B 2017/1139* (2013.01); *A61F 2002/041* (2013.01); *A61F 2002/8483* (2013.01); *A61F 2002/9511* (2013.01); *A61F 2210/009* (2013.01); *A61F 2230/0039* (2013.01); *A61F 2230/0095* (2013.01); *A61F 2250/0039* (2013.01); *A61M 2025/0233* (2013.01); *A61M 2025/0286* (2013.01)

(58) Field of Classification Search
  CPC ........ A61F 2002/9511; A61F 2021/009; A61F 2230/0039
  See application file for complete search history.

(56) References Cited

U.S. PATENT DOCUMENTS

| | | | |
|---|---|---|---|
| 5,425,739 A | 6/1995 | Jessen | |
| 5,709,713 A | 1/1998 | Evans et al. | |
| 5,893,856 A | 4/1999 | Jacob et al. | |
| 6,074,416 A | 6/2000 | Berg et al. | |
| 6,113,609 A | 9/2000 | Adams | |
| 6,371,965 B2 | 4/2002 | Gifford et al. | |
| 6,391,036 B1 | 5/2002 | Berg et al. | |
| 6,468,303 B1 | 10/2002 | Amplatz et al. | |
| 6,616,675 B1 | 9/2003 | Evard et al. | |
| 6,620,122 B2 | 9/2003 | Stinson et al. | |
| 8,337,388 B2* | 12/2012 | Vardi | A61B 17/0401 600/37 |
| 8,926,545 B2* | 1/2015 | Brenneman | A61B 17/083 604/8 |
| 2003/0120292 A1 | 6/2003 | Park et al. | |
| 2003/0216770 A1 | 11/2003 | Persidsky et al. | |
| 2004/0044364 A1 | 3/2004 | DeVries et al. | |
| 2004/0249335 A1 | 12/2004 | Faul et al. | |
| 2005/0149166 A1* | 7/2005 | Schaeffer | A61F 2/915 623/1.13 |
| 2008/0249562 A1 | 10/2008 | Cahill | |
| 2009/0062841 A1 | 3/2009 | Amplatz et al. | |
| 2009/0105733 A1 | 4/2009 | Coleman et al. | |
| 2009/0187214 A1 | 7/2009 | Amplatz et al. | |
| 2012/0226243 A1 | 9/2012 | Di Carlo et al. | |
| 2013/0012939 A1* | 1/2013 | Iki | A61B 18/18 606/41 |
| 2013/0012969 A1 | 1/2013 | Shin | |
| 2013/0231689 A1 | 4/2013 | Binmoeller et al. | |
| 2013/0253546 A1* | 9/2013 | Sander | A61B 17/3468 606/151 |
| 2014/0236064 A1* | 8/2014 | Binmoeller | A61B 17/1114 604/8 |
| 2014/0303444 A1 | 10/2014 | Carter | |
| 2016/0015394 A1 | 1/2016 | Cedro, Jr. et al. | |
| 2016/0346453 A1 | 4/2016 | McGuckin et al. | |
| 2016/0135941 A1 | 5/2016 | Binmoeller et al. | |
| 2016/0324633 A1 | 11/2016 | Gross et al. | |

FOREIGN PATENT DOCUMENTS

| | | |
|---|---|---|
| WO | 2014130850 | 8/2014 |
| WO | 2015168508 | 5/2015 |

* cited by examiner

| Time t₀ (minutes) | Temp. T for CEM 43 of 40 minutes (°C) | Temp Elevation over 37°C |
|---|---|---|
| 1 | 45.7 | 8.7 |
| 6 | 44.4 | 7.4 |
| 11 | 43.9 | 6.9 |
| 16 | 43.7 | 6.7 |
| 21 | 43.5 | 6.5 |
| 26 | 43.3 | 6.3 |
| 31 | 43.2 | 6.2 |
| 36 | 43.1 | 6.1 |
| 50 | 42.8 | 5.8 |
| 60 | 42.7 | 5.7 |
| 90 | 42.4 | 5.4 |
| 120 | 42.2 | 5.2 |
| 140 | 42.1 | 5.1 |
| 160 | 42.0 | 5.0 |
| 1000 | 40.7 | 3.7 |
| 5000 | 39.5 | 2.5 |
| 10000 | 39.0 | 2.0 |

| Time t₀ (minutes) | Temp. T for CEM 43 of 40 minutes (°C) | Temp Elevation over 37°C |
|---|---|---|
| 0.1 | 47.3 | 10.3 |
| 5.1 | 44.5 | 7.5 |
| 10.1 | 44.0 | 7.0 |
| 15.1 | 43.7 | 6.7 |
| 20.1 | 43.5 | 6.5 |
| 25.1 | 43.3 | 6.3 |
| 30.1 | 43.2 | 6.2 |
| 35.1 | 43.1 | 6.1 |
| 50 | 42.8 | 5.8 |
| 60 | 42.7 | 5.7 |
| 90 | 42.4 | 5.4 |
| 120 | 42.2 | 5.2 |
| 140 | 42.1 | 5.1 |
| 160 | 42.0 | 5.0 |
| 1000 | 40.7 | 3.7 |
| 5000 | 39.5 | 2.5 |
| 10000 | 39.0 | 2.0 |

For T > 43°C    $t_0 = t_{43} \, 2^{(43-T)}$
For T < 43°C    $t_0 = t_{43} \, 4^{(43-T)}$ $T = 43 - \log_2(t_0/40) = 43 - [(\ln(t_0/40)/(\ln(2))]$
$T = 43 - \log_4(t_0/40) = 43 - [(\ln(t_0/40)/(\ln(2))]$ $$C = \sum_{k=0}^{n} \binom{n}{k} t_i^{-1} R^{43-T_i}$$

CEM 43 CALCULATIONS

FIG. 8

SYSTEMS AND METHODS FOR CREATING PERMANENT DRAINAGE FISTULA

CROSS REFERENCE TO RELATED APPLICATIONS

The present application claims the benefit of priority under 35 U.S.C. § 119 to U.S. Provisional Application Ser. No. 62/522,348, filed on Jun. 20, 2017, the disclosure of which is incorporated by reference in its entirety for all purposes.

FIELD

The present disclosure relates generally to the field of medical devices and establishing fluid communication between body lumens. In particular, the present disclosure relates to devices and methods for establishing a permanent open flow or access passage between body lumens.

BACKGROUND

The desire to establish access to body lumens to create fluid communication from one to the other is present under various circumstances and conditions. A variety of medical devices (e.g., drainage stents, etc.) are able to establish open flow or access passages between body lumens. These medical devices are generally not indicated for long-term use, and are often removed from the patient within weeks or months after placement. Once the medical device has been removed, the rapidly replenishing cells of the mucosal layer of each body lumen may inherently close or seal the opening (e.g., fistula, anastomosis, etc.). While this self-sealing ability may be advantageous in certain circumstances, various medical conditions require a long term or permanent opening to be maintained between the body lumens after the anastomotic device has been removed from the patient.

For example, blockage of bile flow from the gallbladder to the common bile duct (CBD) causes accumulation of bile within the gallbladder, leading to jaundice in the short term and potentially life-threatening consequences in the long term. Commercially available drainage devices (e.g., Axios™ Stent, Boston Scientific Corporation) may be placed to provide relief from acute cholecystitis by draining bile and/or gallstones from the gallbladder to the duodenum. Since these drainage devices are not indicated for permanent implantation, the standard of care for treating chronic cholecystitis is gallbladder removal. Approximately 800,000 gallbladder removal procedures are performed each year in the U.S alone.

A variety of advantageous medical outcomes may be realized by the devices and/or methods of the present disclosure, for example, placing the tissue walls of first and second body lumens in direct contact such that the apposed muscularis layers fuse together to form a long term or permanent open flow or access passage that prevents or significantly inhibits closure or sealing.

SUMMARY

In one aspect, the present disclosure relates to a medical device comprising an elongate body forming a lumen and including a proximal portion, a distal portion, a length and a diameter. The elongate body may include an elongate tubular configuration, and a foreshortened configuration where the proximal portion may expand into a proximal retention member and the distal portion may expand into a distal retention member leaving a cylindrical saddle region therebetween. A plurality of proximal tissue-engaging elements may be disposed along an outer surface of the cylindrical saddle region distal to the proximal retention member, and a plurality of distal tissue-engaging elements may be disposed along an outer surface of the cylindrical saddle region proximal to the distal retention member. A first end of each proximal tissue-engaging element may be attached to the outer surface of the cylindrical saddle region, and a second end of each proximal tissue-engaging element may be unattached and extend toward the distal retention member. A first end of each distal tissue-engaging element may be attached to the outer surface of the cylindrical saddle region, and a second end of each distal tissue-engaging element may be unattached and extend toward the proximal retention member. The unattached second end of each proximal tissue-engaging element may be elevated about the outer surface of the cylindrical saddle region. The unattached second end of each distal tissue-engaging element may be elevated about the outer surface of the cylindrical saddle region. The unattached second end of each proximal tissue-engaging element may be configured to penetrate a tissue wall of a first body lumen. The unattached second end of each distal tissue-engaging element may be configured to penetrate a tissue wall of a second body lumen. The plurality of proximal and/or distal tissue-engaging elements may lay flat against the outer surface of the elongate body when in the elongate tubular configuration. A surface of the proximal retention member may be configured to contact an inner surface of a tissue wall of a first body lumen, and a surface of the distal retention member may be configured to contact an inner surface of a tissue wall of a second body lumen. The tissue walls of the first and second body lumens may be apposed between the proximal and distal retention members along the cylindrical saddle region. A portion of the tissue wall of the first body lumen engaged by the plurality of proximal tissue-engaging elements may deflect along the cylindrical saddle region toward the distal retention member, and a portion of the tissue wall of the second body lumen engaged by the plurality of distal tissue-engaging elements may deflect along the cylindrical saddle region toward the proximal retention member, thereby placing a tissue layer (e.g., muscularis layer) of the tissue wall of the first body lumen in contact with a tissue layer (e.g., muscularis layer) of the tissue wall of the second body lumen.

In another aspect, the present disclosure relates to a medical device comprising an elongate body forming a lumen and comprising a proximal portion, a distal portion, a length and a diameter. The elongate body may include an elongate tubular configuration, and a foreshortened configuration where the proximal portion may expand into a proximal retention member and the distal portion may expand into a distal retention member leaving a cylindrical saddle region therebetween. A first magnet may be disposed within proximal retention member, and a second magnet may be disposed within the distal retention member. An attractive force between the first and second magnets may urge the proximal and distal retention members toward each other. A surface of the proximal retention member may be configured to contact an inner surface of a tissue wall of a first body lumen, and a surface of the distal retention member may be configured to contact an inner surface of a tissue wall of a second body lumen. The tissue walls of the first and second body lumens may be apposed between the proximal and distal retention members along the cylindrical saddle region. The surface of the proximal retention member may cause necrosis within the tissue wall of the first body lumen, and the surface of the distal retention member may cause necrosis within the tissue wall of the second body lumen. The necrosis within the tissue walls of the first and second body lumens may expose and place a healthy tissue layer (e.g., muscularis layer) of the first and second body lumens in contact with each other.

In another aspect, the present disclosure relates to a medical device comprising an elongate body forming a lumen and comprising a proximal portion, a distal portion, a length and a diameter. The elongate body may include an elongate tubular configuration, and a foreshortened configuration where the proximal portion may expand into a proximal retention member and the distal portion may expand into a distal retention member leaving a cylindrical saddle region therebetween. A filament may be threaded through a portion of the elongate body to effectuate compression of the proximal and distal ends toward each other. For example, a first end of the filament may be attached to a proximal end of the medical device at a first location, a second end of the filament may be unattached and extend from the proximal end of the medical device at a second location, and a portion of the filament between the first and second ends may form a loop extending along the cylindrical saddle region between the proximal and distal retention members. Proximally retracting the second end of the filament may urge the proximal and distal retention members toward each other. The medical device may further include a locking member attached to the elongate body adjacent to the second location. The locking member may be configured to secure a portion of the filament. A surface of the proximal retention member may be configured to contact an inner surface of a tissue wall of a first body lumen, and a surface of the distal retention member may be configured to contact an inner surface of a tissue wall of a second body lumen. The tissue walls of the first and second body lumens may be apposed between the proximal and distal retention members along the cylindrical saddle region. The surface of the proximal retention member may cause necrosis within the tissue wall of the first body lumen, and the surface of the distal retention member may cause necrosis within the tissue wall of the second body lumen. The necrosis within the tissue walls of the first and second body lumens may expose and place a healthy tissue layer (e.g., muscularis layer) of the first and second body lumens in contact with each other.

In another aspect, the present disclosure relates to a medical device comprising an elongate body forming a lumen and comprising a proximal portion, a distal portion, a length and a diameter. The elongate body may include an elongate tubular configuration, and a foreshortened configuration where the proximal portion may expand into a proximal retention member and the distal portion may expand into a distal retention member leaving a cylindrical saddle region therebetween. The medical device may become heated in the presence of energy, including MRI energy, and cause necrosis within the tissue walls of the first and second body lumens. The necrosis within the tissue walls of the first and second body lumens may expose and place a healthy tissue layer (e.g., muscularis layer) of the first and second body lumens in contact with each other.

In another aspect, the present disclosure relates to a medical device comprising a first flexible member which includes an inner surface, an outer surface and a first opening extending therebetween, and second flexible member comprising an inner surface, an outer surface and a second opening therebetween. A plurality of tabs may extend from the inner surface of the second flexible member, and a plurality of recesses may be formed within the inner surface of the first flexible member. Each recess of the first flexible member may be configured to receive a corresponding tab of the second flexible member such that the first and second openings may align to form a combined opening. The inner surface of the first flexible member and the inner surface of the second flexible member may be separated by a distance when the plurality of tabs may be received within the plurality of recesses. The plurality of tabs may be configured to penetrate the tissue walls of a first and second body lumen. The plurality of tabs may be configured to extend through an opening between the tissue walls a first and second body lumen.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIG. 8 provides calculations and equations for radiofrequency induced heating of an implanted medical, according to one embodiment of the present disclosure.

DETAILED DESCRIPTION

The present disclosure is not limited to the particular embodiments described. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to medical devices (e.g., stents, etc.) and systems for drainage of the gallbladder, it should be appreciated that such medical devices may be used in a variety of medical procedures (e.g., external biliary drain conversion, enteroenterostomy, gastrojejumostomy, gastroduodenostomy and gastroileostomy, etc.) to establish and/or maintain a temporary or permanent open flow or drainage passage from or between a variety of body organs, lumens, ducts, vessels, fistulas, cysts and spaces (e.g., the dermis, stomach, duodenum, jejunum, small intestine, gallbladder, kidneys, pancreas, biliary/pancreatic trees, bladder, ureter, abscesses, walled-off pancreatic necrosis (WOPN), bile ducts, etc.). The devices can be inserted via different access points and approaches, e.g., percutaneously, endoscopically, laparoscopically or some combination thereof. The medical devices disclosed herein are self-expanding, but in other embodiments the medical device may be expandable by other means, including, e.g., a balloon catheter. Moreover, such medical devices are not limited to drainage, but may facilitate access to organs, vessels or body lumens for other purposes, such as creating a path to divert or bypass fluids or solids from one location to another, removing obstructions and/or delivering therapy, including non-invasive or minimally invasive manipulation of the tissue within the organ and/or the introduction of pharmacological agents via the open flow passage.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

Figure 1:
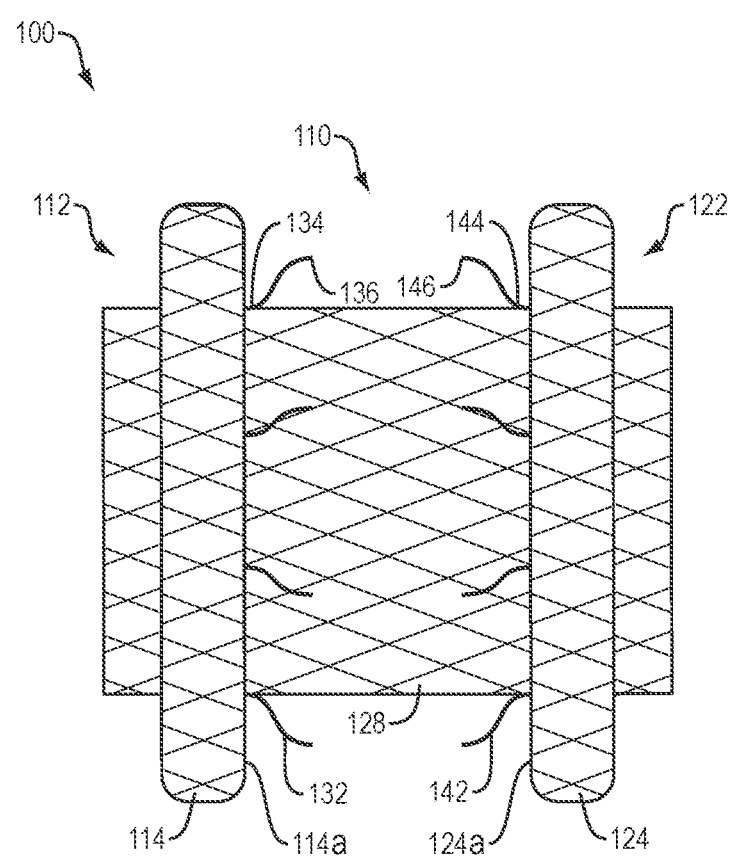
FIG. 1 provides a perspective view of a medical device, according to one embodiment of the present disclosure.

In one embodiment, the present disclosure relates to a medical device (e.g., self-expanding drainage stent, etc.) configured to extend between first and second body lumens and align the respective muscularis layers of each body lumen to establish a long term or permanent open flow or access passage therebetween. Referring to FIG. 1, in one embodiment, a medical device 100 of the present disclosure may include an elongate body 110 forming a lumen and comprising a proximal portion, a distal portion, a length and a diameter. The elongate body 110 may include an elongate tubular configuration (e.g., constrained, unexpanded or delivery configuration; not shown), and a foreshortened configuration (e.g., unconstrained, expanded or deployed configuration) where the proximal portion 112 radially expands into a proximal retention member 114, and the distal portion 122 radially expands into a distal retention member 124, leaving a cylindrical saddle region 128 extending therebetween. A diameter of the cylindrical saddle region 128 may be greater than a diameter of the elongate body 110 in the elongate tubular configuration. The proximal and distal retention members 114, 124 may extend perpendicular to a circumference of the elongate body 110 to define respective planar surfaces 114a, 124a. In various embodiments, the angle of the retention members relative to the circumference of the elongate body may assume other degrees or may change degrees along the retention members creating inflection points in the retention members. A plurality of proximal tissue-engaging elements 132 may be disposed along an outer surface of the cylindrical saddle region 128 at a location distal to the proximal retention member 114, and a plurality of distal tissue-engaging elements 142 may be disposed along an outer surface of the cylindrical saddle region 128 at a location proximal to the distal retention member 124. A first end 134 of each of the proximal tissue-engaging elements 132 may be attached to the outer surface of the cylindrical saddle region 128, and a second end 136 of each of the proximal tissue-engaging elements 134 may be unattached (e.g., free) and extend towards the distal retention member 124. A first end 144 of each of the distal tissue-engaging elements 142 may be attached to the outer surface of the cylindrical saddle region 128, and a second end 146 of each of the distal tissue-engaging elements 142 may be unattached (e.g., free) and extend towards the proximal retention member 114. In the elongate tubular configuration, the proximal and distal tissue-engaging elements 132, 142 may be disposed along (e.g., lay flat against) an outer surface of the elongate body. As the elongate body moves to the foreshortened configuration, the proximal and distal tissue-engaging elements 132, 142 may deflect outward to extend along and above the outer surface of the cylindrical saddle region 128 (e.g., substantially parallel to, or at an acute angle, relative to a longitudinal axis of the cylindrical saddle region).

In various embodiments, the first end 134, 144 of any or all of the first and second tissue-engaging elements 132, 142 may be affixed to the outer surface of the cylindrical saddle region 128 using a suitable glue, adhesive, resin or other bonding techniques, as are commonly known in the art. In addition, or alternatively, the proximal and/or distal tissue-engaging elements 132, 142 may be formed as extensions or projections of the woven, knitted or braided filament comprising the elongate body 110. Any of second ends 136, 146 of the proximal and distal tissue-engaging elements 132, 142 may be sharpened, pointed or otherwise configured to penetrate the tissue wall of a respective first or second body lumen, as discussed below. In addition, any of the proximal and distal tissue-engaging elements 132, 142 may further include one or more barbs, hooks, fingers and/or teeth, etc. configured to secure the tissue-engaging element(s) within the tissue wall of the respective first or second body lumen.

Although the proximal and distal tissue-engaging elements 132, 142 of FIG. 1 are depicted as evenly spaced about an outer circumference of the cylindrical saddle region 128 and immediately adjacent to the respective proximal and distal retention members 114, 124, in various embodiments, the proximal and/or distal tissue-engaging elements 132, 142 may include a variety of shapes, sizes, numbers, orientations, patterns and/or spacing along the cylindrical saddle region. In addition, or alternatively, in various embodiments the tissue-engaging elements are not limited to the cylindrical saddle region, but may be positioned on or along the proximal and/or distal retention members, including the planar tissue-facing surfaces.

In one embodiment, a medical device 100 of the present disclosure may be positioned within a patient such that the proximal and distal tissue-engaging elements 132, 142 reorient a portion of the respective first and second body lumens as the medical device moves from the elongate tubular to foreshortened configuration to place the muscularis layers of the first and second body lumens in contact along an outer surface of the cylindrical saddle region 128. Referring to FIGS. 2A-2F, in use and by way of example, a medical device 100 of the present disclosure may be disposed in the elongate tubular configuration within the lumen of a tissue-penetrating element 10. A sharpened distal end 12 of the tissue-penetrating element 10 may be advanced through the tissue wall 191 of a first body lumen 190 (e.g., the stomach or duodenum) and through the tissue wall 196 of a second body lumen 195 (e.g., the gallbladder).

In various embodiments, the tissue penetrating element 10 may be advanced over a guidewire 16 previously advanced through the first and second body lumens such that a distal end of the guidewire is disposed within the second body lumen. Alternatively, in the method above, a separate instrument with a sharpened distal tip may be advanced along the path above and into the second body lumen to create a path. A guidewire is put in place, or left in place if used to guide the separate instrument, and the separate instrument is withdrawn over the guidewire. A medical device, according to the various embodiments described above, loaded on a delivery catheter, may be inserted over the guidewire, and the medical device then deployed according to the steps outlined above.

Figure 2A:
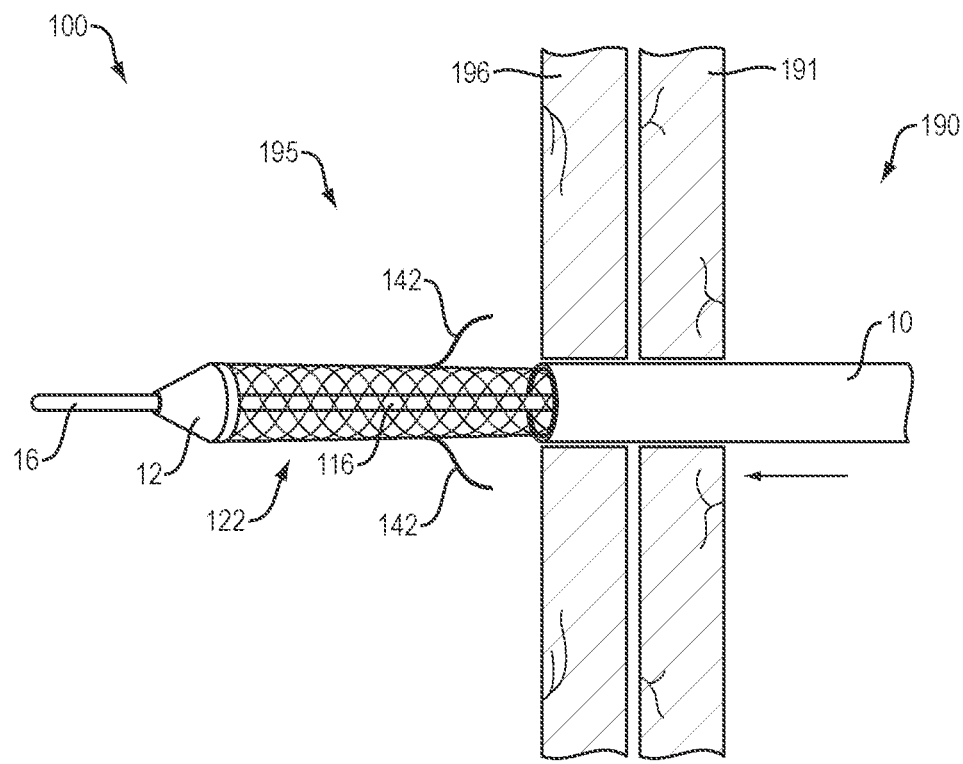
FIGS. 2A-2F illustrate exemplary steps for placement of a medical device between first and second body lumens, according to one embodiment of the present disclosure.
Figure 2B:
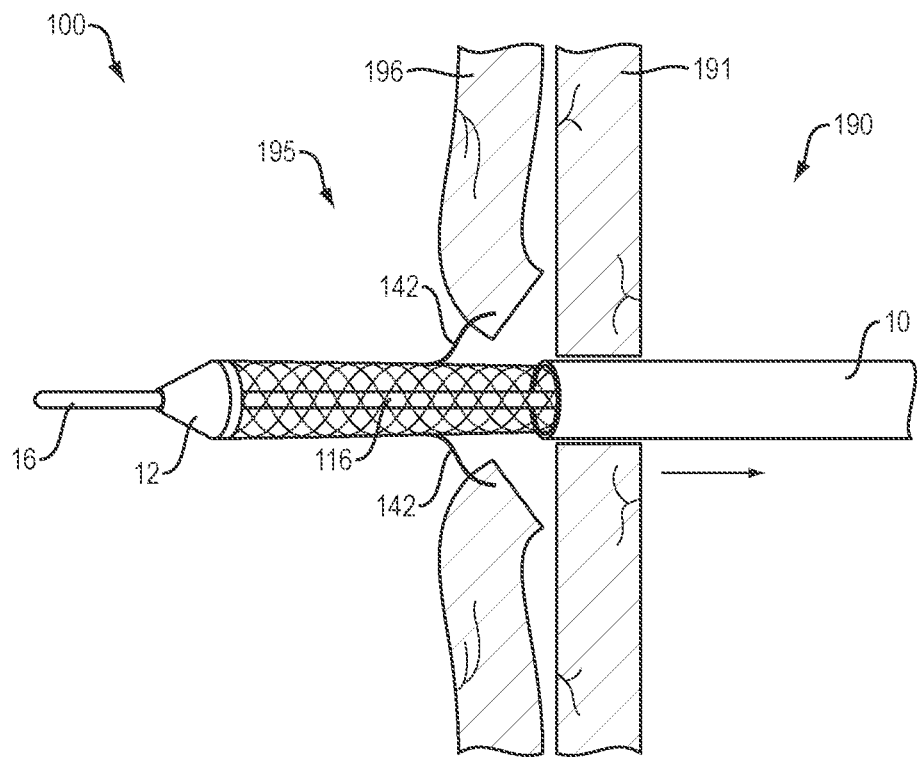

Referring to FIG. 2A, a distal portion 122 of the medical device 100 may then be advanced distally beyond the lumen of the tissue-penetrating element 10 such that the distal tissue-engaging elements 142 are deployed, e.g., removed from constraint within the lumen of the tissue penetrating element 10. Referring to FIG. 2B, the tissue-penetrating element 10 may then be proximally retracted such that at least some of the distal tissue-engaging elements 142 engage (e.g., pierce or penetrate) a portion of the tissue wall 196 of the second body lumen 195 adjacent to the opening formed by the sharpened distal end 12. As the tissue-penetrating element 10 is further proximally retracted, a portion of the tissue wall 196 of the second body lumen 195 may be reoriented, e.g., deflected or turned toward the tissue wall 191 of the first body lumen 190.

Figure 2C:
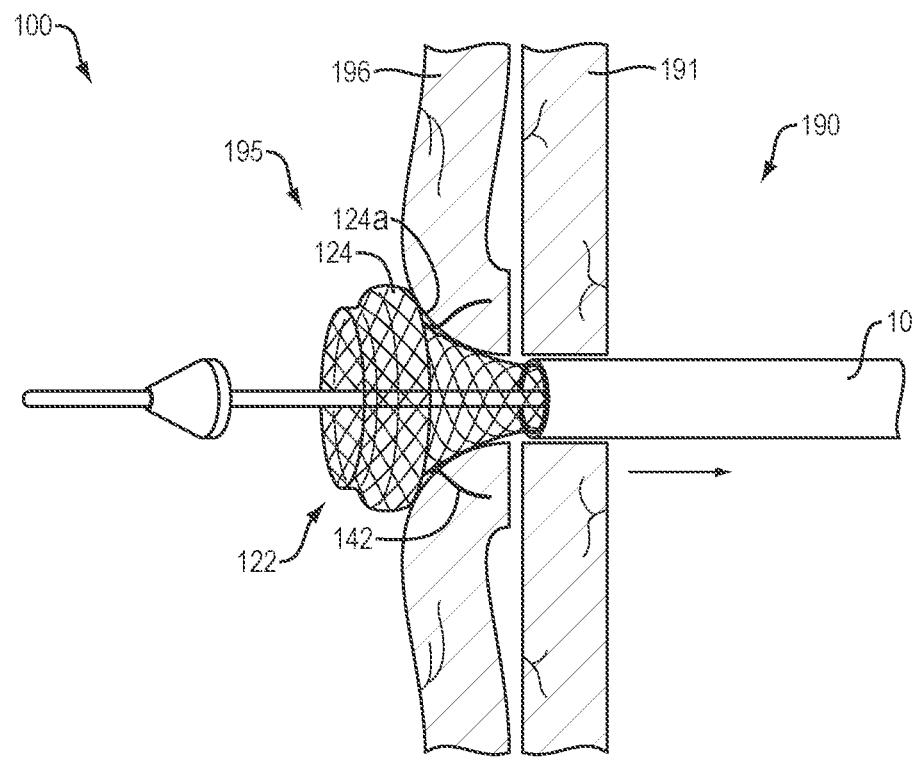
Figure 2D:
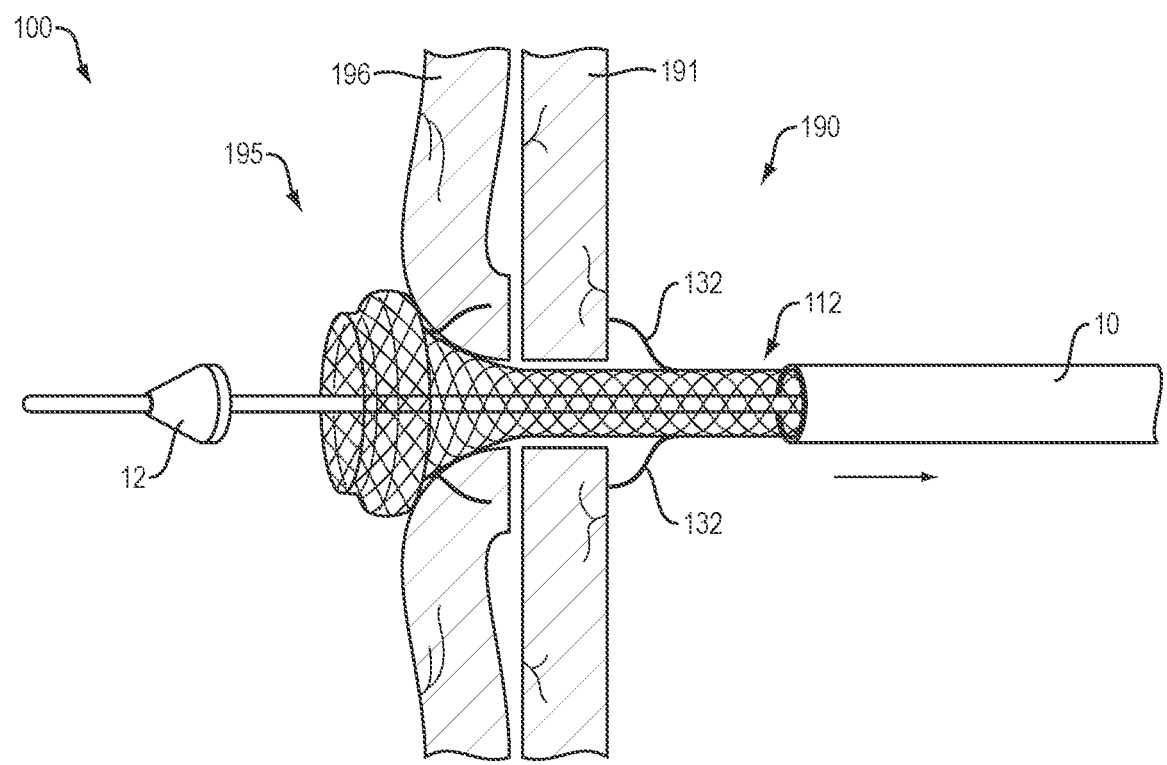
Figure 2E:
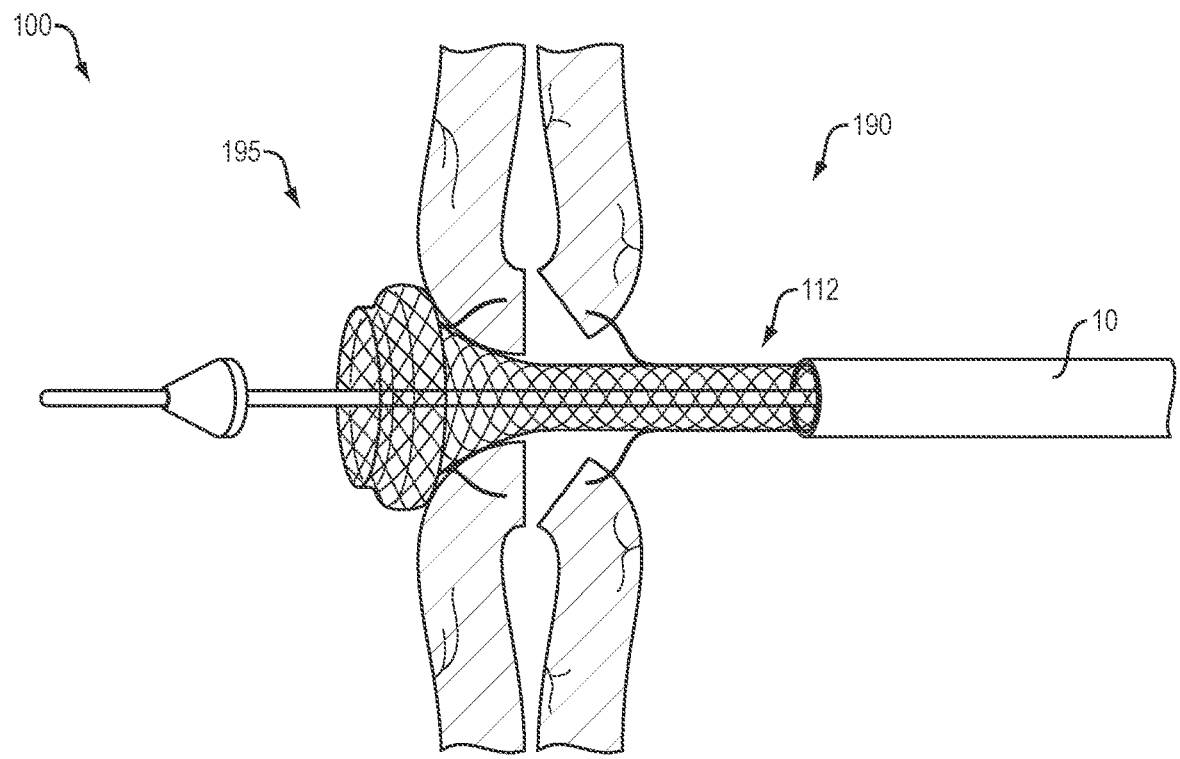
Figure 2F:
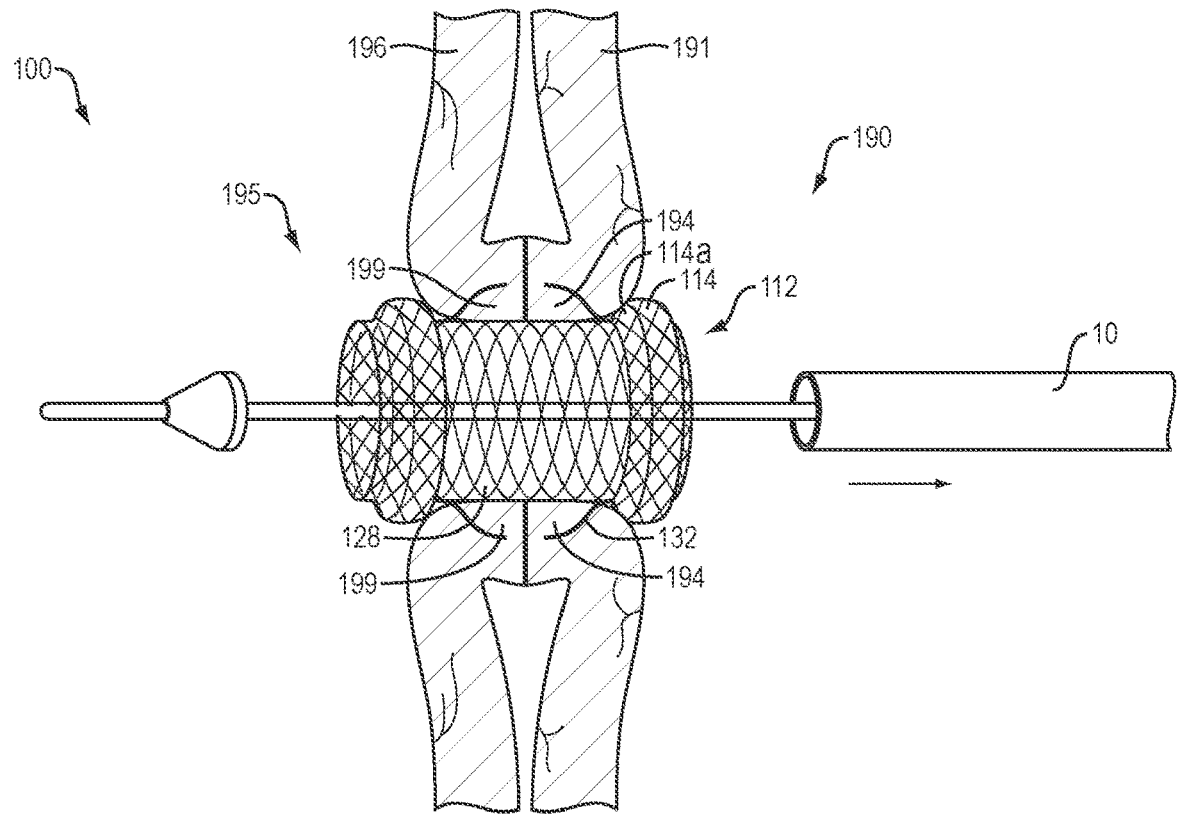

Referring to FIG. 2C, the distal portion 122 of the medical device 100 may then be further advanced distally beyond the lumen of the tissue-penetrating element 10 such that the distal retention member 124 is fully deployed within the second body lumen 195 and the planar surface 124a is placed in contact with the inner surface of the tissue wall 196. Still referring to FIG. 2C, as the distal retention member 124 and a portion of the cylindrical saddle region 128 are deployed from within the tissue-penetrating element 10, the portion of the tissue wall 196 of the second body lumen 195 engaged by the distal tissue-engaging elements 142 may be further reoriented to face the tissue wall 191 of the first body lumen 190. Referring to FIGS. 2D and 2E, the tissue-penetrating element 10 may then be further proximally retracted into the first body lumen 190, and a proximal portion 112 of the medical device 100 advanced distally beyond the lumen of the tissue-penetrating element 10 such that the proximal tissue-engaging elements 132 are deployed, e.g., removed from constraint within the lumen of the tissue penetrating element 10, and placed in contact with a portion of the tissue wall 191 of the first body lumen 190 adjacent to the opening formed by the sharpened distal end 12. Referring to FIG. 2F, the proximal portion 112 of the medical device 100 may then be further advanced distally beyond the lumen of the tissue-penetrating element 10 such that the proximal retention member 114 is fully deployed within the first body lumen 190 and the planar surface 114a is placed in contact with the inner surface of the tissue wall 191. In one embodiment, as the proximal retention member 114 and remaining portion of the cylindrical saddle region 128 are deployed from within the tissue-penetrating element 10, the portion of the tissue wall 191 of the first body lumen 195 engaged by one or more of the proximal tissue-engaging elements 132 may be reoriented to face the previously reoriented tissue wall 196 of the second body lumen 195, thereby placing the respective muscularis layers 194, 199 of the first and second body lumens 190, 195 in contact along the cylindrical saddle region 128.

In various embodiments, the proximal and distal tissue-engaging elements 132, 142 may be sufficiently flexible or deformable to allow the medical device 100 to be removed from the patient without causing substantial trauma to the respective tissue layers. In addition, or alternatively, any or all of the proximal and distal tissue-engaging elements may be formed from a biodegradable or bioerodible material configured to dissolve after the muscularis layers 194, 199 have fused, thereby allowing the medical device to be more easily removed from the patient.

Figure 3B:
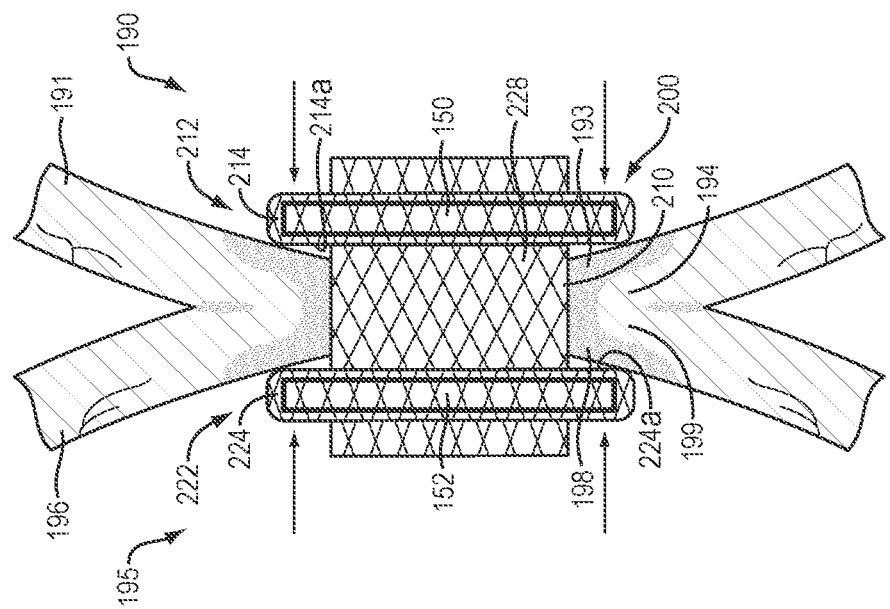
FIGS. 3A-3B provide a perspective view of a medical device disposed between first and second body lumens, according to one embodiment of the present disclosure.
Figure 3A:
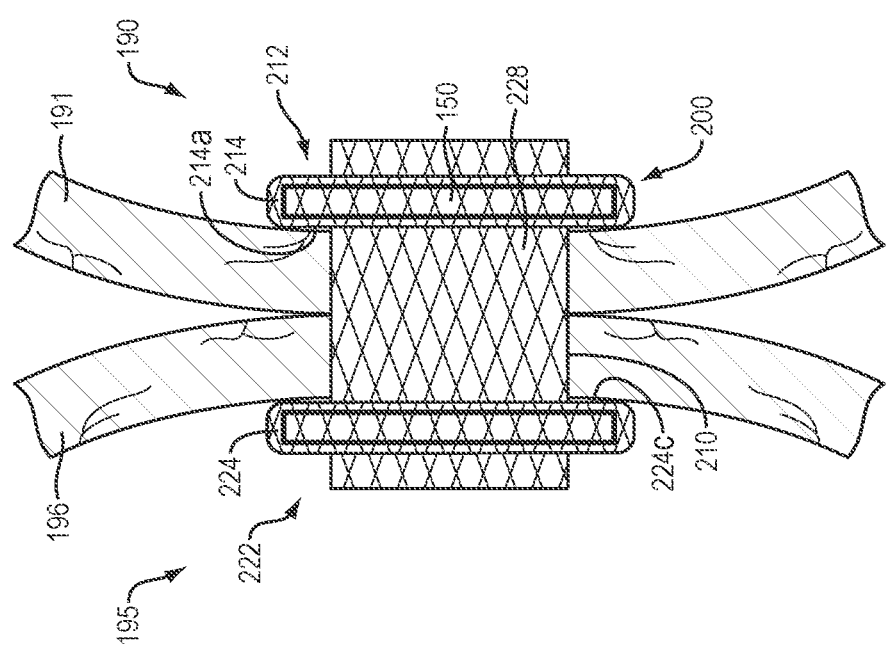

In one embodiment, a medical device 200 of the present disclosure may be positioned within a patient such that the proximal and distal retention members cause selective and localized tissue necrosis of the first and second body lumens to expose adjacent portions of the muscularis layer of each body lumen along an outer surface of the cylindrical saddle. Referring to FIGS. 3A-3B, in one embodiment, a medical device 200 of the present disclosure may include an elongate body 210 forming a lumen and comprising a proximal portion 212, a distal portion 222, a length and a diameter. The elongate body 210 may include an elongate tubular configuration (e.g., constrained, unexpanded or delivery configuration; not shown), and a foreshortened configuration (e.g., unconstrained, expanded or deployed configuration) where the proximal portion 212 radially expands into a proximal retention member 214, and the distal portion 222 radially expands into a distal retention member 224, leaving a cylindrical saddle region 228 extending therebetween. A diameter of the cylindrical saddle region 228 may be greater than a diameter of the elongate body 210 in the elongate tubular configuration. The proximal and distal retention members 214, 224 may extend perpendicular to a circumference of the elongate body 210 to define respective planar surfaces 214a, 224a. A first magnet 150 may be disposed within the proximal retention member 214, and a second magnet 152 may be disposed within the distal retention member 224. The first and second magnets 150, 152 may be disposed within the respective first and second retention members 214, 224 such that the polarities of each magnet provide an attractive force therebetween about a full circumference (e.g., 360 degrees) of the cylindrical saddle region 228. As discussed in greater detail below, the medical device 200 may be disposed between first and second body lumens 190, 195 such that the planar surface 214a of the proximal retention member 214 contacts and presses against the tissue wall 191 of the first body lumen 190, and the planar surface 224a of the distal retention member 224 contacts and presses against the tissue wall 196 of the second body lumen 195 to place the body lumens in contact along the cylindrical saddle region 228 (FIG. 3A). In one embodiment, the attractive force between the first and second magnets 150, 152 may urge the proximal and distal retention members 214, 224 toward each other, thereby shortening the cylindrical saddle region 228 and providing constant and consistent pressure between the planar surfaces 214a, 224a and the respective inner surfaces of each tissue wall 191, 196. In addition, the outer surfaces of each tissue wall may also be compressed against each other between the proximal and distal retention members 214, 224. The constant and consistent pressure exerted on the inner and outer surfaces of each tissue wall 191, 196 may cause selective and localized necrosis at a specific depth of each tissue layer. For example, the depth of necrosis of the first and second tissue walls 191, 196 may be limited to the mucosal layers 193, 198 to selectively expose and place in contact free ends of the muscularis layers 194, 199 along the cylindrical saddle region 228.

Figure 4A:
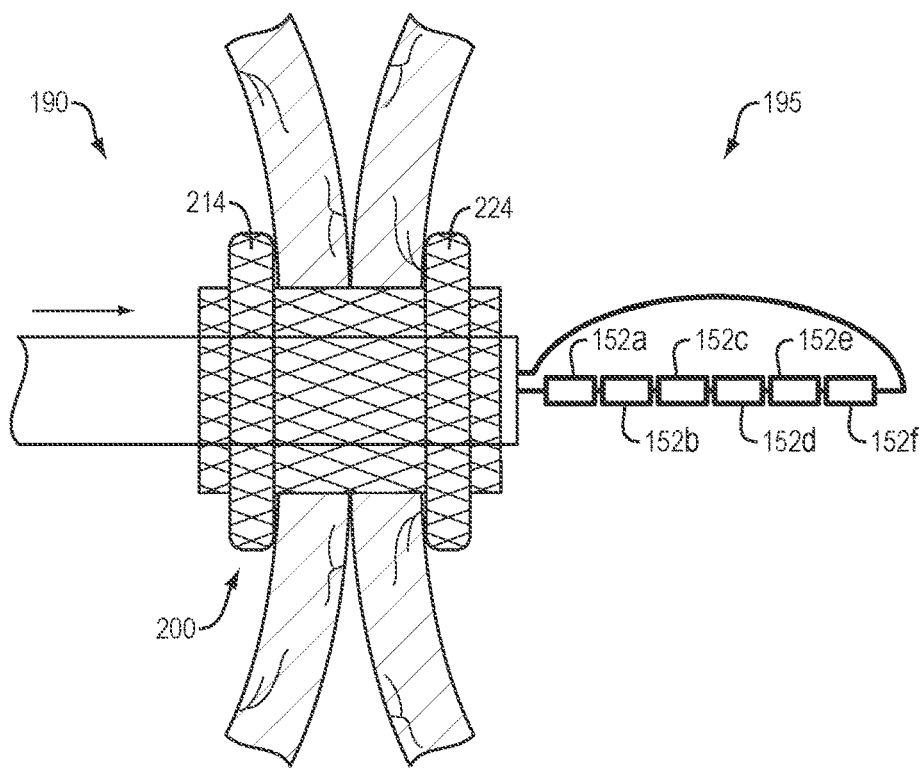
FIGS. 4A-4D illustrate exemplary steps for the placement of magnets within the proximal and distal retention members of a medical device, according to one embodiment of the present disclosure.
Figure 4B:
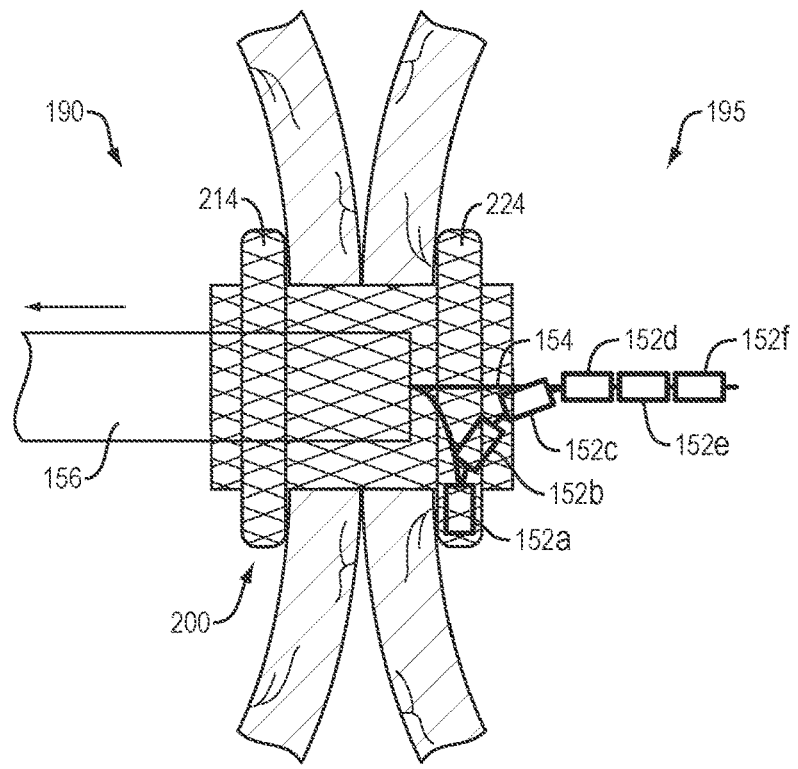
Figure 4C:
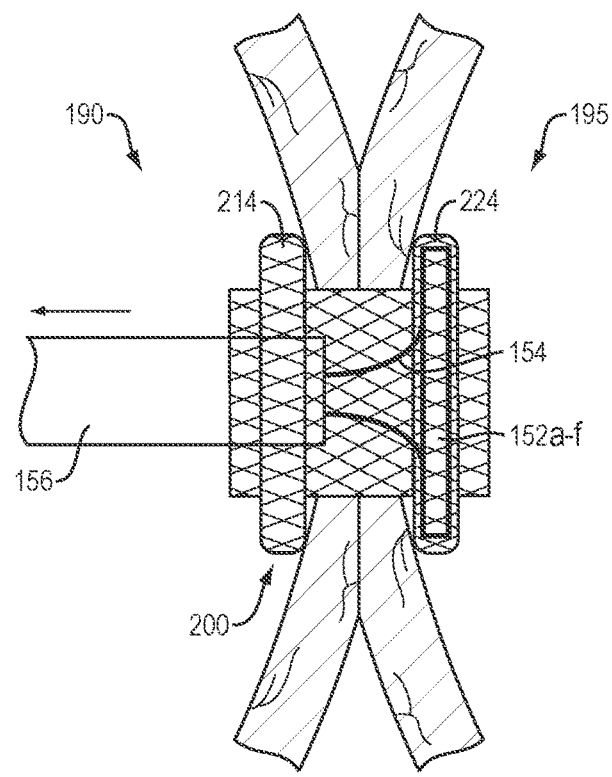
Figure 4D:
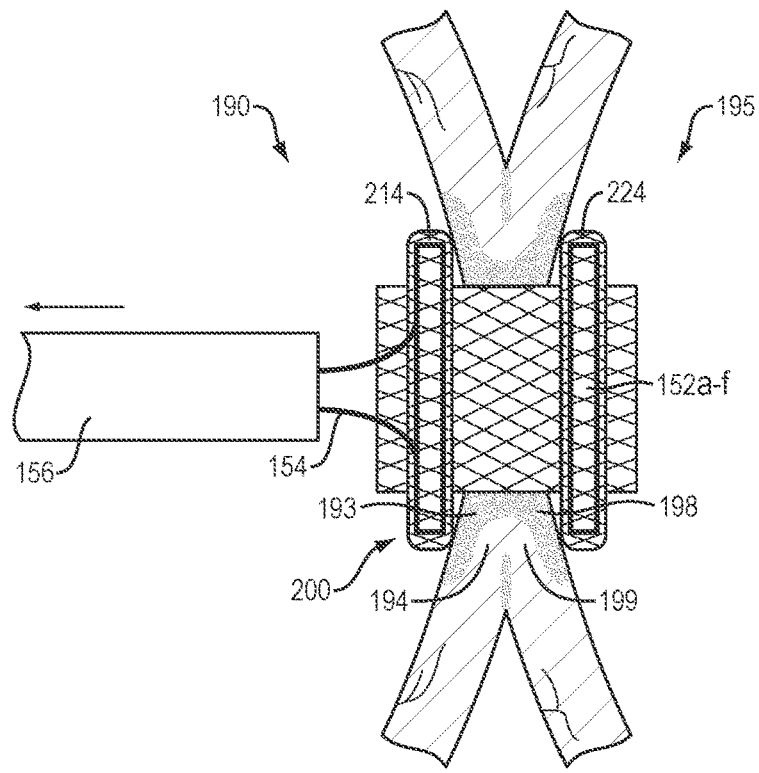
Figure 5A:
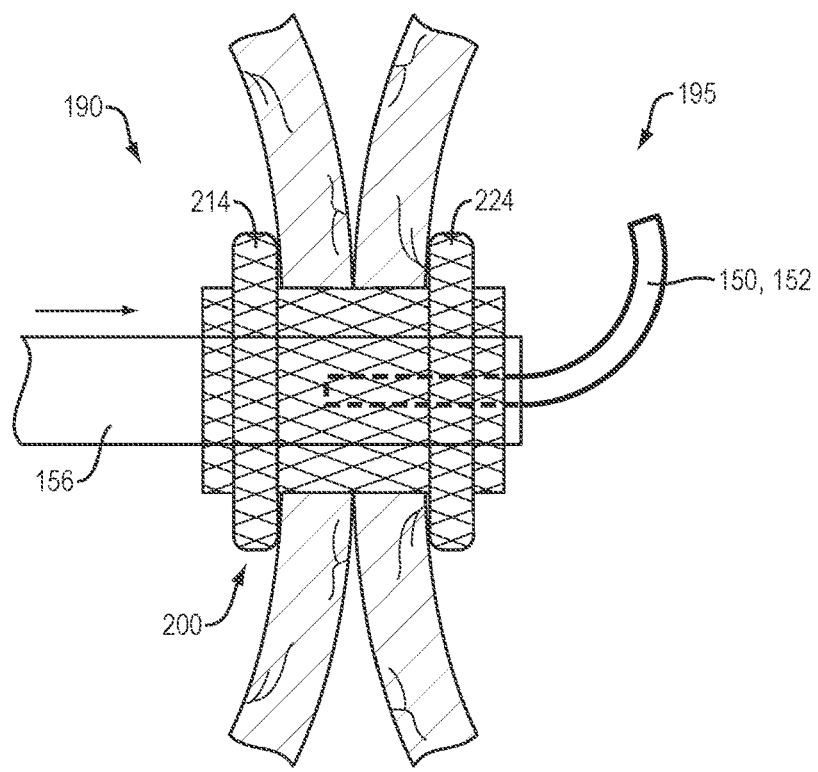
FIGS. 5A-5D illustrate exemplary steps for the placement of magnets within the proximal and distal retention members of a medical device, according to one embodiment of the present disclosure.
Figure 5B:
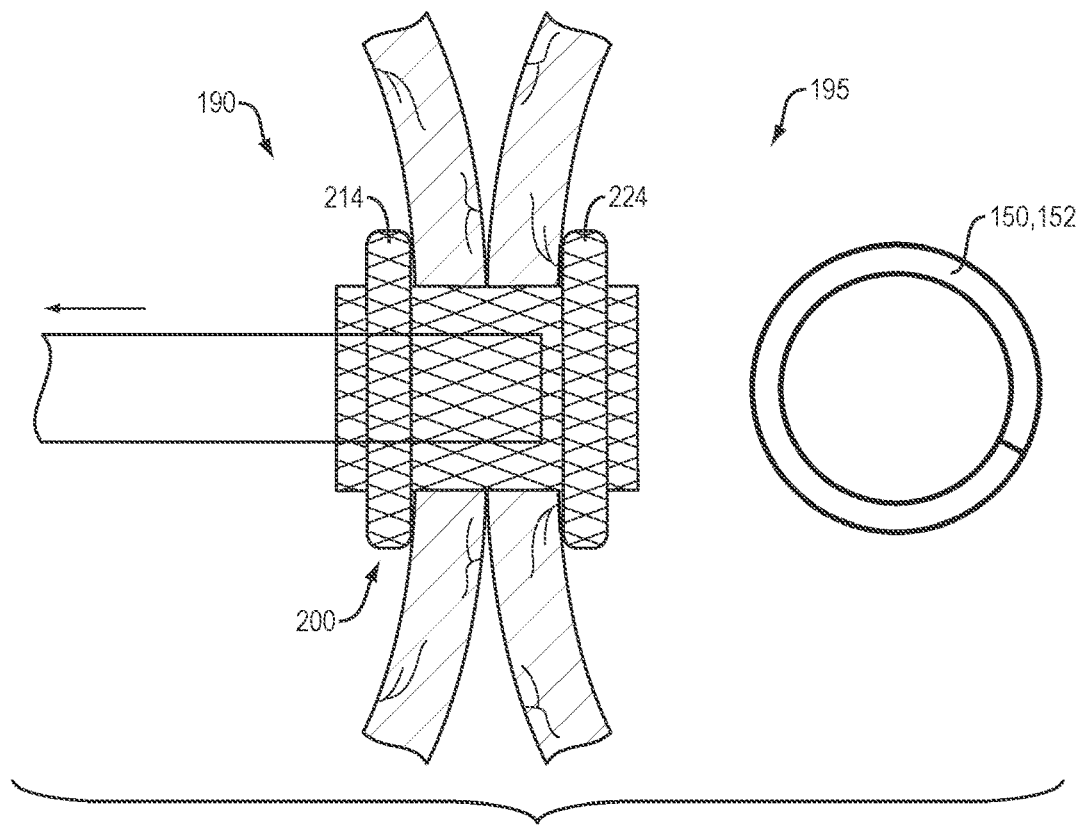
Figure 5C:
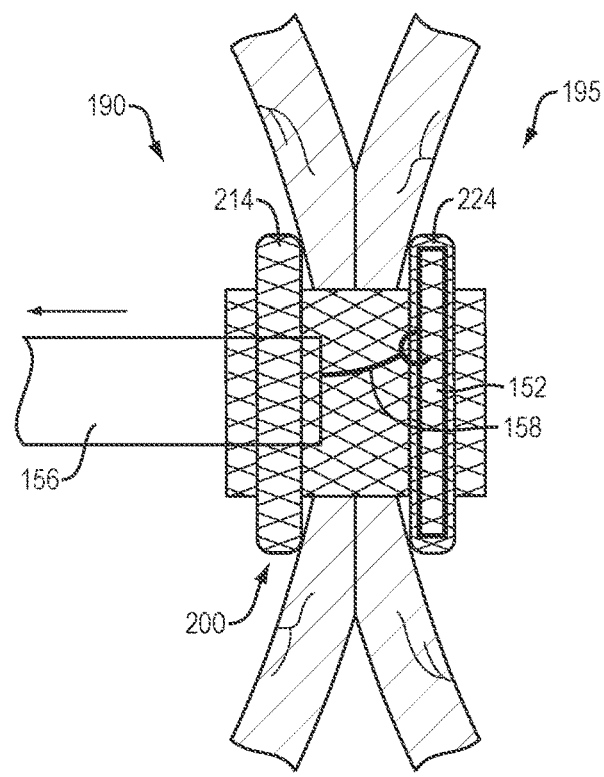
Figure 5D:
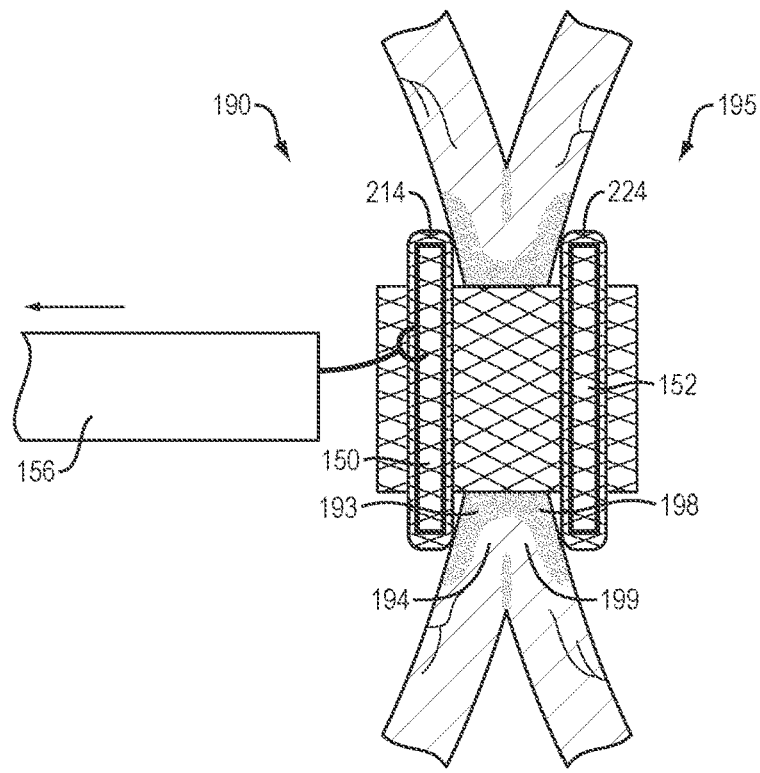

In one embodiment, the medical device 200 may be positioned between the first and second body lumens by following the exemplary steps outlined in FIGS. 2A-2F, as discussed above, with the exception that the tissue walls 191, 196 of the first and second body lumens 190, 195 are placed in contact along the cylindrical saddle region 228, e.g., the respective tissue walls are not reoriented by proximal and distal tissue-engaging elements. Referring to FIGS. 4A-4D, in one embodiment, each of the first and second magnets 150, 152 may include a series of magnet fragments 150a-f, 152a-f loaded onto a delivery wire 154. With the medical device 200 properly positioned between the first and second body lumens 190, 195, a delivery device 156 (e.g., endoscope, etc.) may be advanced into the second body lumen 195 through the lumen of the medical device 200. The delivery wire 154, loaded with a series of magnet fragments 152a-f, may be advanced through the delivery device 156 into the second body lumen 195. The delivery device 156 may then be proximally retracted (FIG. 4A) into the medical device 200, and a proximal and distal end of the delivery wire 154 proximally retracted such that the exposed magnetic fragments 152a-f, e.g., disposed outside the delivery device 156, sequentially snap or fall into place within the open inner circumference of the distal retention member 224 (FIGS. 4B-4C. With the magnetic fragments 152a-f disposed within the distal retention member 224, one end of the delivery wire 154 may be released while the other end is proximally retracted to remove the delivery wire 154 from the medical device 200. This process may be repeated to place magnetic fragments 150a-f within the proximal retention member 214 (FIG. 4D). With the magnetic fragments 150a-f, 152a-f fully deployed within the proximal and distal retention members 214, 224, selective tissue necrosis of the mucosal layers 193, 198, and fusion of the muscularis layers 194, 199 may proceed as discussed above. Referring to FIGS. 5A-5D, in one embodiment, each of the first and second magnets 150, 152 may include a flexible magnet configured to move between a restrained (e.g., linear) configuration and an unconstrained (e.g., non-linear or circular) configuration. With the medical device 200 properly positioned between the first and second body lumens 190, 195, a delivery device 156 (e.g., endoscope) may be advanced into the second body lumen 195 through the lumen of the medical device 200 (FIG. 5A). The flexible magnet 152 may be advanced through the delivery device 156 into the second body lumen, such that the magnet 152 moves to the nonconstrained configuration (FIG. 5B). A medical tool 158 (e.g., grasper, etc.) may be passed through the endoscope to grasp and pull the flexible magnet 152 into the medical device. The flexible magnet 152 may deform as it enters the lumen of the medical device and expand (e.g., snap) into the distal retention member 224 as the medical tool is proximally retracted (FIG. 5C). This process may be repeated to place the flexible magnet 150 within the proximal retention member 214 (FIG. 5D). With the flexible magnets 150, 152 fully deployed within the proximal and distal retention members 214, 224, selective tissue necrosis of the mucosal layers 193, 198, and fusion of the muscularis layers 194, 199 may proceed as discussed above.

In various embodiments, one or more magnets may be positioned on or adjacent to (e.g., alongside) the proximal and/or distal retention members to promote selective tissue necrosis of the mucosal layers, and fusion of the muscularis layers. In other embodiments, magnets may be used in retention members of these devices and other devices to help maintain adjacent tissue layers in apposition for drainage, without the magnets necessarily causing necrosis and fusion.

Figure 6B:
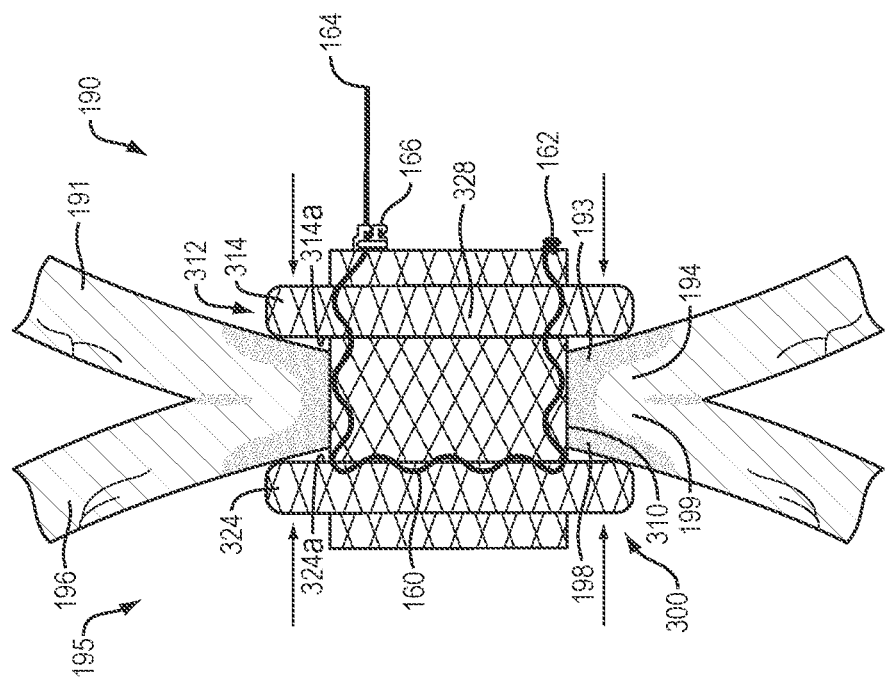
FIGS. 6A-6B provide perspective views of a medical device disposed between first and second body lumens, according to one embodiment of the present disclosure.
Figure 6A:
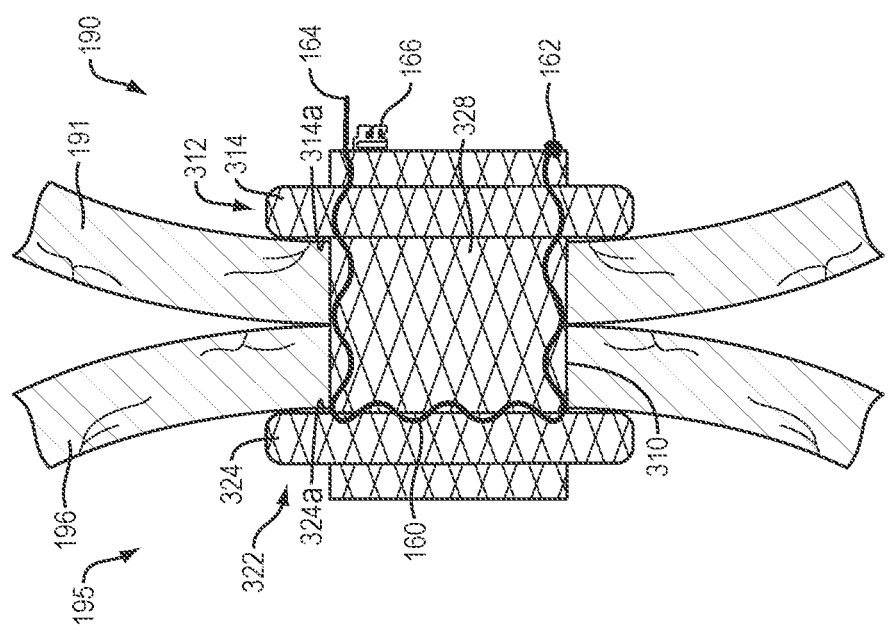

Referring to FIGS. 6A-6B, in one embodiment, a medical device 300 of the present disclosure may include an elongate body forming a lumen and comprising a proximal portion, a distal portion, a length and a diameter. The elongate body 310 may include an elongate tubular configuration (e.g., constrained, unexpanded or delivery configuration; not shown), and a foreshortened configuration (e.g., unconstrained, expanded or deployed configuration) where the proximal portion 312 radially expands into a proximal retention member 314, and the distal portion 322 radially expands into a distal retention member 324, leaving a cylindrical saddle region 328 extending therebetween. A diameter of the cylindrical saddle region 328 may be greater than a diameter of the elongate body 310 in the elongate tubular configuration. The proximal and distal retention members 314, 324 may extend perpendicular to a circumference of the elongate body 310 to define respective planar surfaces 314a, 324a. A filament 160 (e.g., suture, thread, nitinol wire, medical grade nylon, etc.) may be threaded through a portion of the elongate body (e.g., through the woven, knitted or braided filament forming the elongate body) such that a first end 162 of the filament 160 is attached to a proximal end of the medical device 300 at a first location (e.g., proximal to the proximal retention member 314), and a second end 164 of the filament 160 is unattached and extends proximally beyond the proximal end of the medical device 300 at a second location different than the first location. For example, the first and second locations may be on substantially opposite sides of the medical device (e.g., separated by 180 degrees). A portion of the filament 160 between the first and second ends 162, 164 may form a loop extending along the cylindrical saddle region 328 between the proximal and distal retention members 314, 324. In various embodiments, the first end 162 of the filament 160 may be affixed to the proximal end of the medical device using a suitable knot, glue, adhesive, resin or other bonding techniques, as are commonly known in the art. In various embodiments, the filament 160 may be configured to slide through the woven, knitted or braided filament which forms the elongate body such that proximally retracting the second end 164 of the filament 160, while the medical device is immobilized (e.g., disposed between first and second body lumens) in the foreshortened configuration, may urge the proximal and distal retention members 314, 324 toward each other, thereby shortening the cylindrical saddle region 328. A locking member 166 (e.g., cleat, tie-off, etc.) may be attached to the medical device adjacent to the second location. In addition, or alternatively, the locking member may be integrally formed from a portion of the filament which forms the elongate body 310. The locking member 166 may be configured to securingly receive/engage a portion of the filament 160 (e.g., loops, windings, etc.) after the second end 164 of the filament 160 has been proximally retracted, thereby maintaining the proximal and distal retention members 314, 324 in the compressed (e.g., further foreshortened) configuration.

In various embodiments, the filament 160 may be proximally retracted and "tied-off" to the locking member 166 to establish the desired amount of pressure to the tissue walls 191, 196 of the first and second body lumens 190, 195, as discussed below. A distance between the proximal and distal retention members 314, 324 (and pressure applied to the respective tissue walls) may be adjusted as necessary by securing different portions of the filament 160 to the locking member 166. For example, additional force may be applied between the respective tissue walls by releasing (e.g., untying) the filament 160 from the locking member 166, further proximally retracting the second end 164 and re-securing the filament 160 to the locking member 166. Similarly, the force applied between the respective tissue walls may be decreased by releasing the filament 160 from the locking member 166, allowing the second end 164 to slide distally and re-securing the filament 160 to the locking member 166. Alternatively, the filament 160 may be released from the locking member 166 and the free end 164 allowed to slide distally without being re-secured to the locking member 166 as a first step in removing the medical device 300 from the patient.

In one embodiment, the medical device 300 may be positioned between the first and second body lumens by following the exemplary steps outlined in FIGS. 2A-2F, as discussed above, with the exception that the tissue walls 191, 196 of the first and second body lumens 190, 195 are placed in contact along the cylindrical saddle region 328, e.g., the respective tissue walls are not reoriented by proximal and distal tissue-engaging elements. With the medical device properly positioned between the first and second body lumens 190, 195, the planar surface 314a of the proximal retention member 314 may contact and press against the tissue wall 191 of the first body lumen 190, and the planar surface 324a of the distal retention member 324 may contact and press against the tissue wall 196 of the second body lumen 195 to place the body lumens in contact along the cylindrical saddle region 328 (FIG. 6A). The second end 164 of the filament 160 may then be proximally retracted (e.g., using a suitable grasping member, etc.) to urge the proximal and distal retention members 314, 324 toward each other and secured to the locking member 166, thereby providing constant and consistent pressure between the planar surfaces 314a, 324a and the respective inner surfaces of each tissue wall 191, 196. In addition, the outer surfaces of each tissue wall may also be compressed against each other between the proximal and distal retention members 314, 324. The constant and consistent pressure exerted on the inner and outer surfaces of each tissue wall 191, 196 may cause selective and localized necrosis at a specific depth of each tissue layer. For example, the depth of necrosis of the first and second tissue walls 191, 196 may be limited to the mucosal layers 193, 198 to selectively expose and place in contact free ends of the muscularis layers 194, 199 along the cylindrical saddle region 328 (FIG. 6B).

Figure 7B:
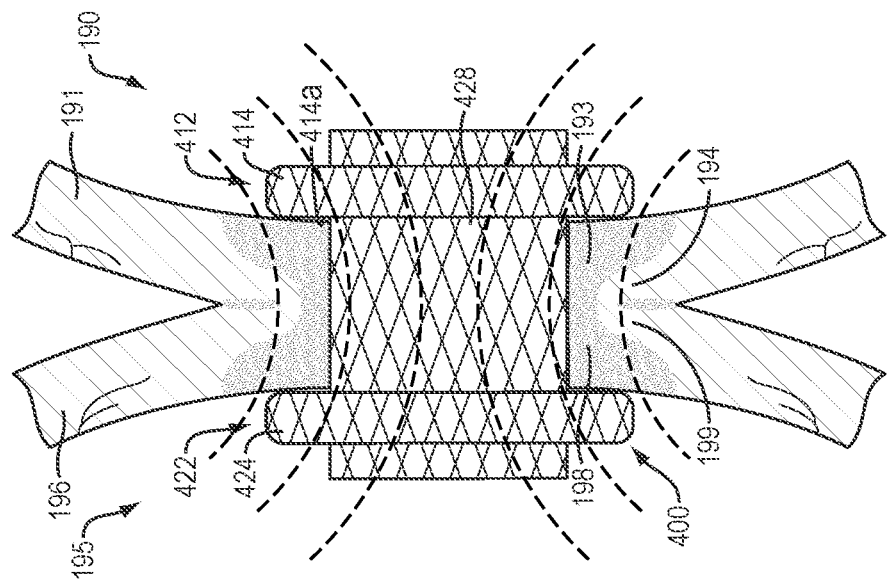
FIGS. 7A-7B provide perspective views of a medical device disposed between first and second body lumens, according to one embodiment of the present disclosure.
Figure 7A:
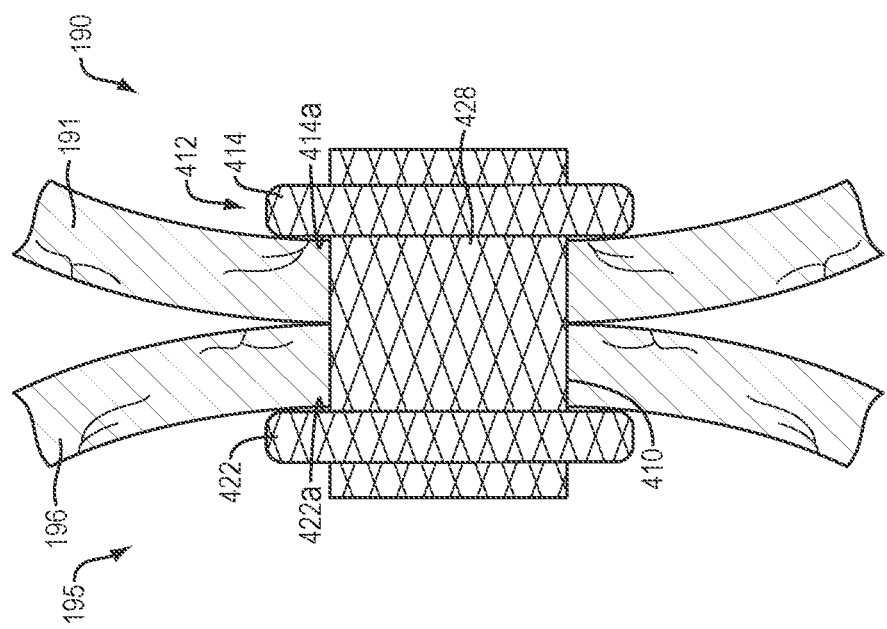

In one embodiment, a medical device 400 of the present disclosure may establish a long term or permanent open flow or access passage without reorienting (e.g., FIG. 1-2F) or compressing (e.g., FIGS. 3A-6B) the tissue walls 191, 196 of the first and second body lumens 190, 195 along the cylindrical saddle region. Referring to FIGS. 7A-7B, in one embodiment, a medical device 400 of the present disclosure may include an elongate body forming a lumen and comprising a proximal portion, a distal portion, a length and a diameter. The elongate body 410 may include an elongate tubular configuration (e.g., constrained, unexpanded or delivery configuration; not shown), and a foreshortened configuration (e.g., unconstrained, expanded or deployed configuration) where the proximal portion 412 radially expands into a proximal retention member 414, and the distal portion 422 radially expands into a distal retention member 424, leaving a cylindrical saddle region 428 extending therebetween. A diameter of the cylindrical saddle region 428 may be greater than a diameter of the elongate body 410 in the elongate tubular configuration. The proximal and distal retention members 414, 424 may extend perpendicular to a circumference of the elongate body 410 to define respective planar surfaces 414a, 424a. The medical device 400 may be positioned between the first and second body lumens by following the exemplary steps outlined in FIGS. 2A-2F, as discussed above, with the exception that the tissue walls 191, 196 of the first and second body lumens 190, 195 are placed in contact along the cylindrical saddle region 428, e.g., the respective tissue walls are not reoriented by proximal and distal tissue-engaging elements. With the medical device properly positioned between the first and second body lumens 190, 195, the planar surface 414a of the proximal retention member 414 my contact and press against the tissue wall 191 of the first body lumen 190, and the planar surface 424a of the distal retention member 424 may contact and press against the tissue wall 196 of the second body lumen 195, to place the body lumens in contact along the cylindrical saddle region 428 (FIG. 7A).

In one embodiment, the medical device 400 may include an amount of ferrous material (e.g., formed within the membrane or coating and/or the woven, knitted or braided filament of the elongate body) such that exposure of the patient to an appropriate magnetic field may cause localized vibration of the medical device 400. Establishing the proper frequency of vibrations within the medical device, e.g., by exposing the medical device to the magnetic field generated by a standard MRI machine, may cause the medical device to heat to an appropriate temperature to selectively kill the cells of the mucosal layer 194, 198 of the first and second body lumens 190, 195. In addition to selectively killing the cells of the mucosal layer 193, 198, and placing the underlying muscularis layers 194, 199 of the first and second body lumens 190, 195 in direct contact, heat emitted from the medical device 400 may also cauterize the exposed tissue surfaces to facilitate fusion of the muscularis layers (FIG. 7B).

Referring to Cumulative Effective Minutes at 43° C. Calculations (CEM 43) of FIG. 8, radiofrequency induced heating of an implanted medical device may cause cell death when the surrounding tissues are exposed to an elevated temperature (e.g., above 37° C.; body temperature) for an extended period of time. For example, in one embodiment, cell death may occur after one minute of exposure of a medical device heated to 45.7° C. (e.g., 8.7° C. above body temperature), or after 160 minutes of exposure to a medical device heated to 42.0° C. (e.g., 5.0° C. over body temperature). Although FIGS. 7A-7B depict a heat-induced open flow or access passage achieved using a medical device 400 that does not include tissue-engaging elements, magnets or slidable filaments, in various embodiments, any or all of the medical devices 100, 200, 300 disclosed herein may also include an MRI-induced heating step to further promote the requisite killing of the cells comprising the mucosal layers and place the adjacent muscularis layers of the first and second body lumens in contact. Similarly, in various embodiments, any of the medical device 100, 200, 300, 400 disclosed herein may include any combination of the elements (e.g., tissue-engaging elements, magnets or slidable filaments, ferrous materials, etc.) disclosed herein.

The elongate body of any of the medical devices 100, 200, 300, 400 depicted in FIGS. 1-7B may be formed of a woven, knitted or braided filament (e.g., nitinol wire, etc.). The proximal retention member, distal retention member and/or cylindrical saddle region may further include a membrane or coating on an inner and/or outer surface thereof to define a contiguous open interior passage configured for flow (e.g., body fluids, materials, and the like) and/or access therethrough. The coating may comprise a variety of non-degradable and biocompatible polymeric materials (e.g., upon exposure to bodily fluids such as bile), including, for example, silicones, rubbers, polyethylenes, PVDF, Chronoflex® and thermoplastic elastomers such that the coating conforms to the medical device in the elongate tubular and foreshortened configurations. In addition, or alternatively, the woven, knitted or braided filament in any of the various embodiments may be metal filament or polymer filament, and may further include a single filament woven upon itself or multiple filaments woven together. In addition, or alternatively, in one embodiment, the open interior passage may further include one or more valves (e.g., duck-bill valve, slit valve, etc.) moveable between closed and open configurations to block or prevent the flow of fluids therethrough, until the patient or medical professional determines that the valve should be opened (e.g., by inserting a drainage tube). These valves may be positioned anywhere along the open interior passage of the elongate body. Examples of such valves are described in U.S. Patent Publication No. 2012/0226243, the contents of which is hereby incorporated by reference in its entirety. Such valves may comprise a variety of suitable biocompatible and non-degradable materials, including any of the polymers discussed herein, and may be utilized with any of the various embodiments described or otherwise contemplated as within the scope of the present disclosure.

The first and second retention members of any of the medical devices 100, 200, 300, 400 depicted in FIGS. 1-7B may include various configurations, such that one or more of the retention members extend radially at an angle that is not necessarily perpendicular to the elongate body and/or the surfaces are not necessarily planar. For example, one or both of the proximal and distal retention members may extend outward towards an end of the elongate body, back towards a center portion of the elongate body, or change directions in some combination of both. In addition, or alternatively, one or both of the proximal and distal retention members may include an outer diameter $d_1$ that is greater than an outer diameter $d_2$ of the cylindrical saddle region. For example, outer diameter $d_1$ may be as much as 75%-100% greater than an outer diameter $d_2$ of the cylindrical saddle region. By way of non-limiting example, outer diameter $d_1$ may be approximately 7.0 mm to approximately 30 mm, and outer diameter $d_2$ may be approximately 3.0 mm to approximately 15.0 mm. In various embodiments, the size (e.g., diameter) of the opening formed between the first and second body lumens may be increased or decreased by increasing or decreasing the size (e.g., width) of the proximal and distal retention members (e.g., increasing or decreasing the surface area of the tissue layers compressed between the proximal and distal retention members). In addition, or alternatively, a length of the elongate body in the foreshortened configuration may be at least 40% shorter than a length of the elongate body when in the elongate tubular configuration.

In various embodiments, any of the medical devices 100, 200, 300, 400 of the present disclosure may remain in place within the patient for a sufficient amount of time for the muscularis layers 194, 195 to join or fuse (e.g., grow together), at which point the medical device may be removed from the patient to leave a long term or permanent open flow, drainage or access passage between the first and second body lumens 190, 195. For example, the medical devices 100, 200, 300, 400 may be maintained within the body for a period of days to weeks to establish the requisite level of tissue necrosis between the proximal and distal retention members. The necrotic tissue may eventually slough off to leave a permanent opening defined by the fused muscularis layers.

In various embodiments, any of the medical devices 100, 200, 300, 400 of the present disclosure may further include one or more chemicals (e.g., silver nitrate) or anti-proliferative agents embedded on or within the coating of the medical device, including, for example, the cylindrical saddle region and/or the planar surfaces of the proximal and distal retention members, to further facilitate selective killing of the cells of the mucosal layer of the first and second body lumens. In addition, or alternatively, once the medical devices of the present disclosure are removed from the patient, a surgical glue, cryocautery or cryoablation treatment may be applied to the inside diameter of the opening between the first and second body lumens to seal the fused muscularis layers and further prevent the ingrowth of mucosal cells.

Figure 9A:
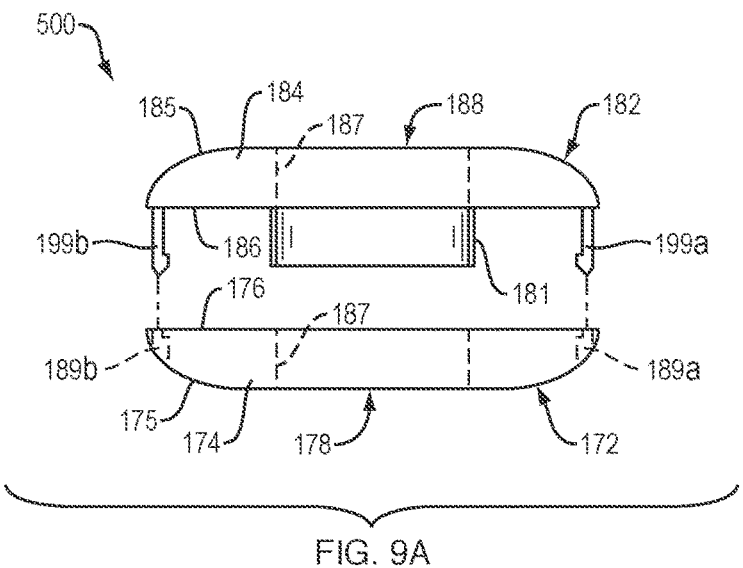
FIGS. 9A-9C provide perspective views of a medical device disposed between first and second body lumens, according to one embodiment of the present disclosure.
Figure 9B:
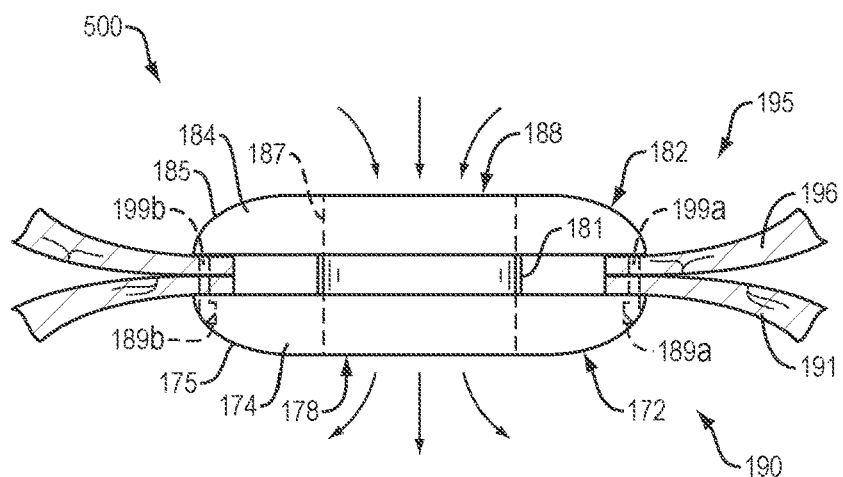

In one embodiment, an opening established between first and second body lumens as described herein may be maintained by replacing the medical device used to establish the opening with a permanent implant (e.g., grommet) configured to physically prevent (e.g., block) the opening from closing or re-sealing. Referring to FIGS. 9A-9B, a medical device 500 of the present disclosure may include interlockable first and second flexible members 172, 182. For example, the first and second flexible members 172, 182 may be formed from a suitable polymeric material (e.g., silicones, rubbers and the like) configured to be deformed, bent, fold, rolled, compressed or otherwise deformed (e.g., within a delivery sheath, etc.) for delivery into a first or second body lumen, and return to the original non-deformed configuration once released from constraint within the respective body lumen. The first flexible member 172 may include an outer surface 174, a substantially flat or planer inner surface 176, an outer edge 175 with a first circumference and an inner edge 177 with a second circumference less than the first circumference, wherein the inner edge 177 defines a first opening 178 extending between the outer and inner surfaces 174, 176. A plurality of recesses 189a, 189b (e.g., two or more) may be formed within the inner surface 176 along the outer edge 175 of the first flexible member 172. The second flexible member 182 may include an outer surface 184, a substantially flat or planer inner surface 186, an outer edge 185 with a first circumference and an inner edge 187 with a second circumference less than the first circumference, wherein the inner edge 187 defines a second opening 188 extending between the outer and inner surfaces 184, 186. A plurality of tabs 199a, 199b (e.g., two or more) may extend from the inner surface 186 along the outer edge 185 of the second flexible member 182. A cylinder 181 coextensive with the second opening 188 may also extend from the inner surface 186 of the second flexible member 182. Each recess 189a, 189b of the first flexible member 172 may be configured to securingly receive a corresponding tab 199a, 199b of the second flexible member 182, e.g., in an interlocking or snap-fit manner, such that the first and second openings 178, 188 align to form a contiguous open lumen defined by the cylinder 181, and with the inner surfaces 176, 186 of the first and second flexible members 172, 182 separated by a predetermined distance.

Referring to FIG. 9B, in use and by way of example, a medical device 500 of the present disclosure may be disposed within a previously formed opening between first and second body lumens 190, 195 by loading the first and second flexible members 172, 182 within the lumen of a delivery tube in a folded or compressed configuration (not shown).

The delivery tube may be advanced through the opening between the first and second body lumens 190, 195 such that a distal end of the delivery tube is disposed within the second body lumen 195. The second flexible member 182 may then be advanced distally beyond the lumen of the delivery tube such that the second flexible member 182 moves to a non-constrained configuration within the second body lumen 195. A separate medical device (not shown) may be advanced through the lumen of the delivery tube, or along an outer surface of the delivery tube, to grasp the second flexible member 182 and place the plurality of tabs 199a, 199b in contact with the tissue wall 196 of the second body lumen 196 such that the second opening 188 aligns with the opening between the first and second body lumens 190, 195. The medical device may then be proximally retracted with sufficient force that the tabs 199a, 199b of the second flexible member 182 penetrate and extend through the tissue walls 191, 196 of the first and second body lumens 190, 195, and the cylinder 181 extends through the opening between the first and second body lumens 190, 195. The delivery tube may then be proximally retracted such that the distal end of the delivery tube is disposed within the first body lumen 190. The first flexible member 172 may then be advanced distally beyond the lumen of the delivery tube such that the first flexible member 172 moves to a non-constrained configuration with the first body lumen 190. While maintaining pressure on the second flexible member 182 with the medical device, the first flexible member 172 may be placed in contact with the tissue wall 191 of the first body lumen 190 such that the first opening 178 aligns with the opening between the first and second body lumens 190, 195, the recesses 189a, 189b on the inner surface 174 of the first flexible member 172 align with the tabs 199a, 199b of the second flexible member 182 extending into the first body lumen 190 and the cylinder 181 extends through the opening between the first and second body lumens 190, 195. In one embodiment, the distal end of the delivery tube may be used to place the first flexible member 172 in contact with the tissue wall 191 of the first body lumen 190. Alternatively, a second medical device (not shown) may be positioned within the first body lumen 190 to grasp the first flexible member 172 and align the recesses 189a, 189b with the respective ends of the tabs 199a, 199b. The first and second flexible members 172, 182 may then be advanced toward each other such that the tabs 199a, 199b extending from the inner surface 186 of the second flexible member 182 engage the corresponding recesses 189a, 189b on the inner surface 176 of the second flexible member 172, thereby aligning the first and second openings 178, 188 of the first and second flexible members 172, 176 with the opening between the first and second body lumens. A predetermined distance between the inner surfaces 176, 186 of the first and second flexible members 172, 182 may allow the tissue walls 191, 196 of the first and second body lumens to be maintained in a non-compressed state (e.g., one that does not induce tissue necrosis) throughout the duration of the medical device being implanted within the patient. Although FIGS. 9A-9B depicts two tabs 199a, 199b and two corresponding recesses 189a, 189b disposed on opposite sides of the ends of their respective flexible members 172, 182, in various embodiments, any number or tabs and recesses may be disposed in a variety of patterns, orientations and/or configurations.

Figure 9C:
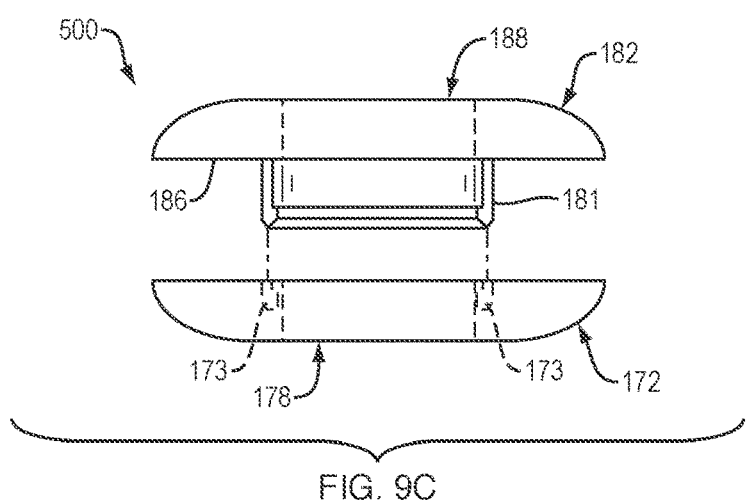

Referring to FIG. 9C, to minimize trauma to the tissue layers of the first and second body lumens, in one embodiment, a medical device 500 of the present disclosure may include interlockable first and second flexible members 172, 182, as discussed above. A cylinder 181 coextensive with the second opening 188 may extend from the inner surface 186 of the second flexible member 182. A free end of the cylinder may include series of tabs (or a single continuous or circular tab) configured to extend through an opening between the first and second body lumens and engage a corresponding recess 173 (e.g., circular groove) surrounding the first opening 178 of the first flexible member 172 in an interlocking or snap-fit manner, such that the first and second openings 178, 188 align to form a contiguous open lumen defined by the cylinder 181, and with the inner surfaces 176, 186 of the first and second flexible members 172, 182 separated by a predetermined distance.

In addition, in various embodiments, the first and second flexible members 172, 182 are not limited to being disposed within the first and second body lumens. For example, the first flexible member may be disposed within the second body lumen to receive the tabs of the second flexible member positioned within the first body lumen.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:
1. A medical device, comprising:
an elongate body forming a lumen and comprising a proximal portion, a distal portion, a length and a diameter;
the elongate body having an elongate tubular configuration, and a foreshortened configuration where the proximal portion expands into a proximal retention member and the distal portion expands into a distal retention member leaving a cylindrical saddle region therebetween;
a plurality of proximal tissue-engaging elements disposed along an outer surface of the cylindrical saddle region distal to the proximal retention member, the proximal tissue-engaging elements comprising free ends extending towards the distal retention member; and
a plurality of distal tissue-engaging elements disposed along an outer surface of the cylindrical saddle region proximal to the distal retention member, the distal tissue-engaging elements comprising free ends extending towards the proximal retention member.

2. The medical device of claim 1, wherein a first end of each proximal tissue-engaging element is attached to the outer surface of the cylindrical saddle region, and a second end of each proximal tissue-engaging element is unattached and extends toward the distal retention member.

3. The medical device of claim 2, wherein the unattached second end of each proximal tissue-engaging element is elevated about the outer surface of the cylindrical saddle region.

4. The medical device of claim 2, wherein the unattached second end of each proximal tissue-engaging element is configured to penetrate a tissue wall of a first body lumen, wherein the unattached second end of each distal tissue-engaging element is configured to penetrate a tissue wall of a second body lumen, or both.

5. The medical device of claim 1, wherein a first end of each distal tissue-engaging element is attached to the outer surface of the cylindrical saddle region, and a second end of each distal tissue-engaging element is unattached and extends toward the proximal retention member.

6. The medical device of claim 5, wherein the unattached second end of each distal tissue-engaging element is elevated about the outer surface of the cylindrical saddle region.

7. The medical device of claim 5, wherein the unattached second end of each distal tissue-engaging element is configured to penetrate a tissue wall of a second body lumen.

8. The medical device of claim 1, wherein a surface of the proximal retention member is configured to contact an inner surface of a tissue wall of a first body lumen, and a surface of the distal retention member is configured to contact an inner surface of a tissue wall of a second body lumen.

9. The medical device of claim 8, wherein the tissue walls of the first and second body lumens are apposed between the proximal and distal retention members along the cylindrical saddle region.

10. The medical device of claim 9, wherein a portion of the tissue wall of the first body lumen engaged by the plurality of proximal tissue-engaging elements deflects along the cylindrical saddle region toward the distal retention member, and a portion of the tissue wall of the second body lumen engaged by the plurality of distal tissue-engaging elements deflects along the cylindrical saddle region toward the proximal retention member, thereby placing a muscularis layer of the tissue wall of the first body lumen in contact with a muscularis layer of the tissue wall of the second body lumen.

11. The medical device of claim 8, wherein the surface of the proximal retention member configured to contact the inner surface of the tissue wall of the first body lumen is a substantially planar surface, or wherein the surface of the distal retention member configured to contact the inner surface of the tissue wall of the second body lumen is a substantially planar surface, or both.

12. The medical device of claim 1, wherein one or both of the proximal retention member and the distal retention member extend substantially perpendicular to a circumference of the cylindrical saddle region.

13. A method of delivering a medical device, comprising:
advancing a tissue-penetrating element from a first body lumen through to a second body lumen, wherein the tissue-penetrating element comprises a lumen and the medical device is disposed within the lumen for delivery, and wherein the medical device comprises an elongate body comprising a proximal portion, a distal portion, and a cylindrical saddle region therebetween;
expanding the distal portion of the medical device into a distal retention member within the second body lumen;
deploying a plurality of distal tissue-engaging elements from constraint within the lumen to extend from the saddle region proximally away from the distal retention member within the second body lumen;
deploying a plurality of proximal tissue-engaging elements from constraint within the lumen to extend from the saddle region distally toward the distal retention member from within the first body lumen; and
expanding the proximal portion of the medical device into a proximal retention member within the first body lumen.

14. The method of claim 13, wherein at least one of the plurality of distal tissue-engaging elements engage an inner surface of a tissue wall of the second body lumen.

15. The method of claim 14, wherein at least one of the plurality of proximal tissue-engaging elements engage an inner surface of a tissue wall of the first body lumen.

16. The method of claim 15, wherein during use a portion of the tissue wall of the first body lumen engaged by the plurality of proximal tissue-engaging elements deflects along the cylindrical saddle region toward the distal retention member, and a portion of the tissue wall of the second body lumen engaged by the plurality of distal tissue-engaging elements deflects along the cylindrical saddle region toward the proximal retention member.

17. The method of claim 13, wherein the proximal and distal tissue-engaging elements comprise terminal ends that are elevated radially from the outer surface of the cylindrical saddle region.

18. The method of claim 13, wherein a surface of the proximal retention member is configured to contact an inner surface of a tissue wall of the first body lumen, and a surface of the distal retention member is configured to contact an inner surface of a tissue wall of the second body lumen.

* * * * *